US011634860B2

(12) United States Patent
Bik et al.

(10) Patent No.: US 11,634,860 B2
(45) Date of Patent: Apr. 25, 2023

(54) ARTICLES AND METHODS FOR DISPENSING METAL IONS INTO LAUNDRY SYSTEMS

(71) Applicant: Applied Silver, Inc., Hayward, CA (US)

(72) Inventors: Russell Bik, Arroyo Grande, CA (US); William Morris, San Francisco, CA (US); James Charles Copeland, Arroyo Grande, CA (US); Robert Babcock, Milpitas, CA (US)

(73) Assignee: Applied Silver, Inc., Hayward, CA (US)

( * ) Notice: Subject to any disclaimer, the term of this patent is extended or adjusted under 35 U.S.C. 154(b) by 0 days.

(21) Appl. No.: 16/099,578

(22) PCT Filed: May 12, 2017

(86) PCT No.: PCT/US2017/032401
§ 371 (c)(1),
(2) Date: Nov. 7, 2018

(87) PCT Pub. No.: WO2017/197260
PCT Pub. Date: Nov. 16, 2017

(65) Prior Publication Data
US 2019/0194865 A1 Jun. 27, 2019

Related U.S. Application Data

(60) Provisional application No. 62/415,222, filed on Oct. 31, 2016, provisional application No. 62/335,510, filed on May 12, 2016.

(51) Int. Cl.
| | | |
|---|---|---|
| *A61L 2/16* | (2006.01) | |
| *D06M 16/00* | (2006.01) | |
| *A01N 59/20* | (2006.01) | |
| *D06M 11/00* | (2006.01) | |
| *C11D 3/02* | (2006.01) | |
| *C11D 3/48* | (2006.01) | |
| *C11D 17/04* | (2006.01) | |
| *A61L 2/238* | (2006.01) | |
| *A61L 2/00* | (2006.01) | |
| *A01N 59/16* | (2006.01) | |
| *D06M 101/06* | (2006.01) | |
| *D06M 101/32* | (2006.01) | |

(52) U.S. Cl.
CPC ............ *D06M 16/00* (2013.01); *A01N 59/16* (2013.01); *A01N 59/20* (2013.01); *A61L 2/00* (2013.01); *A61L 2/16* (2013.01); *A61L 2/238* (2013.01); *C11D 3/02* (2013.01); *C11D 3/48* (2013.01); *C11D 17/046* (2013.01); *D06M 11/00* (2013.01); *D06M 2101/06* (2013.01); *D06M 2101/32* (2013.01)

(58) Field of Classification Search
CPC ........................................................ A61L 2/16
See application file for complete search history.

(56) References Cited

U.S. PATENT DOCUMENTS

| | | |
|---|---|---|
| 4,710,282 A | 12/1987 | Chak et al. |
| 4,755,268 A | 7/1988 | Matsuo et al. |
| 4,937,273 A * | 6/1990 | Okuyama ............ C08K 3/015 |
| | | 521/119 |
| 5,202,045 A | 4/1993 | Karpusiewicz et al. |
| 5,632,904 A | 5/1997 | Samad et al. |
| 6,037,319 A | 3/2000 | Dickler et al. |
| 6,136,776 A | 10/2000 | Dickler et al. |
| 6,294,186 B1 | 9/2001 | Beerse et al. |
| 6,303,039 B1 | 10/2001 | Back et al. |
| 6,448,212 B1 | 9/2002 | Holderbaum et al. |
| 6,468,950 B1 | 10/2002 | Kawasaki et al. |
| 6,583,176 B2 | 6/2003 | Arata |
| 6,624,130 B2 | 9/2003 | Giblin et al. |
| 6,641,829 B1 | 11/2003 | Green et al. |
| 6,699,826 B1 | 3/2004 | Saijo et al. |
| 6,730,648 B2 | 5/2004 | Gorlin et al. |
| 6,736,936 B1 | 5/2004 | Weston et al. |
| 6,762,157 B1 | 7/2004 | Babinski et al. |
| 6,838,095 B2 | 1/2005 | Newman et al. |
| 6,927,201 B2 | 8/2005 | Hsu et al. |
| 6,946,433 B2 | 9/2005 | Green et al. |
| 6,958,313 B2 | 10/2005 | Caswell et al. |
| 7,012,053 B1 | 3/2006 | Barnabas et al. |
| 7,105,478 B2 | 9/2006 | Guzmann et al. |
| 7,220,715 B2 | 5/2007 | Ghosh et al. |

(Continued)

FOREIGN PATENT DOCUMENTS

| | | |
|---|---|---|
| CA | 162326 S | 1/2016 |
| CN | 1434729 A | 8/2003 |

(Continued)

OTHER PUBLICATIONS

Turner. Metal based antimicrobial strategies. Microbial Biotechnology vol. 10(5); Sep. 2017. (Year: 2017).*
Swicofil, Magic Blue Ball, http://web.archive.org/web/20071028122117/http://www.swicofil.com/bluemagicball_presentation_english.pdf, Oct. 28, 2007.
International Search Report and Written Opinion for PCT/US2017/032401, 9 pages, dated Jul. 31, 2017.
"Antimicrobial AlphaSan RC 2000: Silver sodium hydrogen zirconium phosphate," Sep. 22, 2017 (Sep. 22, 2017), p. 1, XP55711339, U.S.A., Retrieved from the Internet: URL:http://hawaii.gov/hdoa/labels/8171.3.pdf [retrieved on Jul. 2, 2020].

*Primary Examiner* — Donald R Spamer
(74) *Attorney, Agent, or Firm* — McDonnell, Boehnen, Hulbert & Berghoff LLP

(57) ABSTRACT

Articles and methods for treating textiles and other materials with an antimicrobial compound during laundry and/or drying cycles. The articles include a porous substrate and a core composition that is releasably associated with the substrate and that includes a metal ion having antimicrobial activity. Methods include the use of the articles in laundry and/or drying cycles to provide antimicrobial treatment of the textiles and materials.

27 Claims, No Drawings

(56) References Cited

U.S. PATENT DOCUMENTS

| | | |
|---|---|---|
| 7,322,065 B2 | 1/2008 | Kim et al. |
| 7,351,683 B2 | 4/2008 | Del Duca et al. |
| 7,375,070 B2 | 5/2008 | Pegelow et al. |
| 7,422,759 B2 | 9/2008 | Kepner et al. |
| 7,481,081 B2 | 1/2009 | Hsu et al. |
| 7,511,007 B2 | 3/2009 | Tichy et al. |
| 7,517,846 B2 | 4/2009 | Gladfelter et al. |
| 7,543,707 B2 | 6/2009 | Miller |
| 7,617,704 B2 | 11/2009 | Iimori et al. |
| 7,624,601 B2 | 12/2009 | Ikemizu et al. |
| 7,638,476 B2 | 12/2009 | Orlich et al. |
| 7,708,896 B2 | 5/2010 | Ooe et al. |
| 7,718,596 B2 | 5/2010 | Briggs et al. |
| 7,763,579 B2 | 7/2010 | Briggs et al. |
| 7,819,127 B1 | 10/2010 | Huffman |
| 7,927,379 B2 | 4/2011 | Cottrell et al. |
| 8,003,589 B2 | 9/2011 | Panandiker et al. |
| 8,163,690 B2 | 4/2012 | Brown et al. |
| 8,173,067 B2 | 5/2012 | Eldred |
| 8,232,238 B2 | 7/2012 | Ochomogo et al. |
| 8,239,990 B2 | 8/2012 | Lim et al. |
| 8,309,506 B2 | 11/2012 | Sunder et al. |
| 8,394,420 B2 | 3/2013 | Kepner et al. |
| 8,449,732 B2 | 5/2013 | Choi |
| 8,460,395 B2 | 6/2013 | Smulowitz et al. |
| 8,476,216 B2 | 7/2013 | Fernandes |
| 8,551,933 B2 | 10/2013 | Parrish et al. |
| 8,563,447 B2 | 10/2013 | Canada et al. |
| 8,664,174 B2 | 3/2014 | Braeckman et al. |
| 8,729,008 B2 | 5/2014 | Begli et al. |
| 8,754,022 B2 | 6/2014 | Zhang et al. |
| 8,815,786 B2 | 8/2014 | Meine et al. |
| 8,809,250 B2 | 9/2014 | Parrish et al. |
| 8,980,816 B2 | 3/2015 | Dreher et al. |
| 9,121,000 B2 | 9/2015 | Burkinshaw et al. |
| 9,132,296 B2 | 9/2015 | Wingfield |
| 9,222,059 B2 | 12/2015 | Germain et al. |
| 9,234,163 B2 | 1/2016 | Miracle |
| 9,253,986 B2 | 2/2016 | King |
| 2002/0023304 A1 | 2/2002 | Chan |
| 2002/0189954 A1 | 12/2002 | Miyazaki et al. |
| 2003/0104969 A1 | 6/2003 | Caswell et al. |
| 2005/0188731 A1 | 9/2005 | Aouad |
| 2006/0051430 A1 | 3/2006 | Arata et al. |
| 2006/0068024 A1 | 3/2006 | Schroeder et al. |
| 2006/0123556 A1 | 6/2006 | Caswell et al. |
| 2006/0123562 A1 | 6/2006 | Ghosh et al. |
| 2006/0233889 A1 | 10/2006 | Burton et al. |
| 2007/0149435 A1 | 6/2007 | Koenig et al. |
| 2007/0163097 A1 | 7/2007 | Metcalfe et al. |
| 2007/0175833 A1 | 9/2007 | Ikeboh et al. |
| 2008/0041117 A1 | 2/2008 | Lee |
| 2008/0131471 A1 | 6/2008 | Kolbe et al. |
| 2008/0147019 A1 | 6/2008 | Song et al. |
| 2008/0256719 A1 | 10/2008 | Radev |
| 2009/0000040 A1 | 1/2009 | Ikemizu |
| 2009/0035342 A1 | 2/2009 | Karandikar et al. |
| 2009/0218266 A1 | 9/2009 | Sawafta et al. |
| 2010/0000268 A1 | 1/2010 | Kohne |
| 2010/0116689 A1 | 5/2010 | Greene |
| 2011/0100838 A1 | 5/2011 | Kim et al. |
| 2011/0200674 A1 | 9/2011 | MacKay |
| 2012/0003326 A1 | 1/2012 | Meine |
| 2012/0192363 A1 | 9/2012 | King |
| 2014/0202943 A1 | 7/2014 | Pradeep et al. |
| 2014/0274859 A1 | 9/2014 | Adamy |
| 2014/0369953 A1 | 12/2014 | Purschwitz et al. |
| 2015/0175724 A1 | 6/2015 | Klostermann et al. |
| 2015/0330020 A1 | 11/2015 | Buskirk et al. |
| 2015/0376550 A1 | 12/2015 | Ohtani et al. |
| 2016/0010041 A1 | 1/2016 | Sivik et al. |
| 2016/0040104 A1 | 2/2016 | Liu et al. |
| 2016/0083900 A1 | 3/2016 | Johnson |
| 2016/0281032 A1 | 9/2016 | Vockenroth et al. |
| 2016/0287741 A1 | 10/2016 | Harris et al. |
| 2016/0340625 A1 | 11/2016 | Scheibel et al. |
| 2021/0237035 A1 | 8/2021 | Gomes et al. |

FOREIGN PATENT DOCUMENTS

| | | |
|---|---|---|
| CN | 2753774 Y | 1/2006 |
| CN | 2780804 Y | 5/2006 |
| CN | 101307555 B | 11/2008 |
| CN | 101646820 A | 2/2010 |
| CN | 1671911 B | 6/2010 |
| CN | 101926363 B | 12/2010 |
| CN | 201738163 U | 2/2011 |
| CN | 101991870 B | 3/2011 |
| CN | 201791121 U | 4/2011 |
| CN | 102165960 A | 8/2011 |
| CN | 202021117 U | 11/2011 |
| CN | 202036069 U | 11/2011 |
| CN | 102395608 A | 3/2012 |
| CN | 102535114 A | 7/2012 |
| CN | 202386643 U | 8/2012 |
| CN | 202430491 U | 9/2012 |
| CN | 101010004 B | 10/2012 |
| CN | 104245781 A | 12/2014 |
| EP | 1134012 A1 | 9/2001 |
| EP | 1276842 B1 | 1/2003 |
| EP | 1881058 A2 | 1/2008 |
| EP | 1927286 A1 | 6/2008 |
| EP | 2045389 A1 | 4/2009 |
| EP | 2631289 B1 | 8/2012 |
| EP | 2499916 A1 | 9/2012 |
| EP | 2674523 A2 | 12/2013 |
| GB | 2498877 A | 7/2013 |
| JP | H06297626 A | 4/1994 |
| JP | 2001062458 A | 3/2001 |
| JP | 2002113288 A | 4/2002 |
| JP | 2003-325385 | * 11/2003 |
| JP | 2008183283 A | 8/2008 |
| JP | 2008279056 A | 11/2008 |
| KR | 20060096652 A | 9/2006 |
| KR | 10-2006-0117875 | 11/2006 |
| RU | 2193528 C2 | 11/2002 |
| TW | I252268 B | 8/2004 |
| TW | 200902790 A | 1/2009 |
| TW | 201013008 A | 4/2010 |
| WO | 1999/039749 A2 | 8/1998 |
| WO | 2004/104153 A1 | 2/2004 |
| WO | WO2006049478 A1 | 5/2006 |
| WO | WO2006050477 A2 | 5/2006 |
| WO | 2006/129982 A1 | 12/2006 |
| WO | 2007/057077 A1 | 5/2007 |
| WO | WO2010002773 A2 | 1/2010 |
| WO | WO2010119022 A1 | 10/2010 |
| WO | 2012/031853 A1 | 8/2011 |
| WO | WO2011103046 A1 | 8/2011 |
| WO | 2012/095665 A2 | 7/2012 |
| WO | 2012/126786 A1 | 9/2012 |
| WO | 2012/142025 A1 | 10/2012 |
| WO | WO2016135344 A1 | 9/2016 |

* cited by examiner

ARTICLES AND METHODS FOR DISPENSING METAL IONS INTO LAUNDRY SYSTEMS

CROSS REFERENCE TO RELATED APPLICATIONS

This application claims the benefit of priority of U.S. Provisional Patent Application No. 62/335,510, filed May 12, 2016, and US Provisional Patent Application No. 62/415,222, filed Oct. 31, 2016, which are hereby incorporated by reference in their entirety.

FIELD

The disclosure relates to the antimicrobial treatment of textiles and other materials. More particularly, the disclosure relates to articles and methods for imparting metal ions into the wash and/or dry cycles of laundry systems for the purpose of anti-microbial treatment of the textiles and materials.

BACKGROUND

The microbial contamination of fabrics or linens used in clothing, bedsheets, towels, pillows, blankets and similar materials can contribute to staining of the textiles, unwanted odor, and the spread of disease. Previous methods of fabric treatment have included fabrics made of materials that contain or are coated with metals such as silver or copper to provide long-lasting anti-microbial protection. However, the antimicrobial efficacy of metalized fabrics declines with each laundering.

SUMMARY

In one aspect, the disclosure is directed to an article including a porous substrate and a core composition that is releasably associated with the substrate and that includes a metal ion having antimicrobial activity. The metal ion may be silver ion or copper ion. The substrate may include a fabric, such as cotton and/or polyester, a sponge, that may be one or more of polyethylene, polypropylene, and polyurethane, or an open cell foam plastic that may include polyethylene, polypropylene and combinations thereof. The open foam cell plastic may have at least one of the following properties: (a) pore size from about 10 $\mu$M to about 50 $\mu$M, and (b) pore density of about 10-30 pores per inch. In some embodiments, the substrate may be moist.

The article of the disclosure may include a hollow enclosure encasing the substrate and including one or more openings that expose the substrate to an environment exterior to the enclosure. The hollow enclosure may include a hard plastic and may be spheroidal or spherical.

In some embodiments, the core composition further may include a second compound that includes a second ion and a second counterion, wherein the dissociation constant of the metal ion and the first counterion is equal to or greater than the dissociation constant of the metal ion and the second counterion. The second counterion may be, for example, nitrate, fluoride, sulfate, carbonate, chloride, bromide, iodide, or sulfide. In addition, the core composition further may include a third compound that includes an adhesive/cohesive material. The substrate may be coated with the third compound.

In another aspect, the disclosure is directed to method for treating a textile. The method include loading the textile and the article of the disclosure into a wash basin containing water, and laundering the textile in the presence of the article. The laundering may include at least one of a wash cycle and a rinse cycle.

In yet another aspect, the disclosure is directed to a method for treating a textile. The method includes loading the textile and the article of the disclosure into a wash basin containing water into a tumble dryer and exposing the textile and the article to at least one of heat and air in the dryer. The method may include drying the textile. In some embodiments, the method includes providing moisture to the substrate of the article before loading the article into the dryer. The textile may be a non-laundered good. Also, the textile and the article may be wet or dry when loaded into the dryer.

DESCRIPTION

The singular forms of the articles "a," "an," and "the" include plural references unless the context clearly indicates otherwise. For example, the term "a compound" or "at least one compound" can include a plurality of compounds, including mixtures thereof.

The disclosure relates to an article including a porous substrate impregnated with a metal ion. The substrate can be added to a wash basin, (i.e. of a conventional washer extractor) or to the drying cycle in tumble drying machine to impart the metal ion to the textiles during the wash or drying cycles.

For instance, in a typical home use laundry and drying system, household textiles, (clothes, sheets, towels, etc.) are laundered in conventional washer extractor and tumble drying machines. Soiled textiles are laundered in wash and rinse cycles in a washing machine and then are moved to the dryer to complete the process. The article according to the disclosure can be added along with the soiled textiles directly into the washer or it may be added along with the clean, wet textiles to the dryer. In some instances, the article is added to the washer and then moved along with textiles into the dryer.

In one aspect, the article includes a substrate for containing a core composition including a metal ion. The substrate is associated with and retains the metal ion until the substrate is added with textiles to a wash basin or conventional washer extractor where the ion is released into the environment of the wash and or drying cycles. Suitable materials for the substrate include materials that are capable of being loaded with metal ion and capable of releasing the ion into the desired environment.

In some embodiments, the substrate includes an open-cell foam plastic, such as, but not limited to, polyethylene, polypropylene and combinations of these materials. Pore sizes may range from about 10 $\mu$M to about 50 $\mu$M. One particular embodiment includes polyurethane with pore densities of about 10-30 pores per inch. As the person of ordinary skill in the art will appreciate, the material destiny (pore sizes) and thickness of the substrate material in combination with the solubility of the compound with which the substrate is impregnated will determine the rate of release (dissolution) for a given laundry water temperature and amount of agitation.

In another embodiment, the substrate may be a sponge. The sponge may be a natural sponge or a synthetic sponge (i.e., a synthetic foam). In some embodiments the sponge is a synthetic sponge comprising, for example, cellulose, silicone, polyurethane, low-density polyether, polyvinyl alcohol, polyester, and the like. In one example, the sponge is a synthetic polyurethane sponge.

In some embodiments, the substrate may be a fabric, e.g., an absorbent fabric such as a woven fabric, a non-woven fabric, or a combination thereof. The fabric may include natural fibers such as, for example, flax, cotton, wool, felt, and the like. The fabric may also include synthetic fibers such as, for example, rayon, acetate, nylon, polyester, spandex, lyocell, and the like. The fabric may be in the form of a single sheet or multiple sheets.

In some embodiments, the article includes a hollow enclosure that encases the porous substrate. For example, the substrate may be surrounded by a hollow enclosure that has one or more openings that expose the substrate to the environment exterior to the enclosure (i.e., the wash or rinse water or the warm air in the dryer). In various aspects, the hollow enclosure can include a plastic that does not degrade in the washer or drying cycles. Such plastics are well known, such as, for example, fluorocarbon resin, polypropylene, polystyrene, polyurethane, and the like. The hollow enclosure may be flexible or inflexible. In some embodiments, the surface of the hollow enclosure is rubberized. In some embodiments, the hollow enclosure may include any material that imparts a level of inflexibility to the hollow enclosure that prevents the substrate from being compressed during the wash or drying cycles.

The hollow enclosure may be any of a number of shapes. In some embodiments, the hollow enclosure is spherical or spheroidal to avoid any sharp edges that can impact the textiles in the washer or dryer. In other embodiments, the hollow enclosure is polyhedral, for example, the hollow enclosure may be octahedral, dodecahedral, icosahedral, etc., and may include rounded edges to avoid any potential for damaging a textile. In some embodiments the hollow enclosure may be shaped in a manner that provides additional benefit to, for example, a textile in a tumble dryer that the article is loaded into therewith. In one example of the article described herein, the hollow enclosure may be a stellated polyhedron, or the surface of the hollow enclosure may include protrusions or spikes, in order to provide a softening effect to a textile in a tumble dryer that the article is loaded into therewith.

The one or more openings of the hollow enclosure may be evenly sized and spaced around the hollow enclosure, may have a size distribution or and/or may localized to one or more sections of the hollow enclosure. In some embodiments, the one or more openings are spherical or they may be extended, linear, and/or narrow openings (i.e., slits). The opening should be of sufficient size to allow free access of the substrate to the wash water or dryer air, but avoid being able to catch or snag any portion of the textile (buttons, zippers, drawstrings, etc.). The opening may include a molded screen or lattice to prevent anything other than water or air from entering the enclosure.

In some embodiments, the hollow enclosure may include, for example, less than 100 openings that are evenly spaced around the enclosure. In other embodiments, the hollow enclosure may include, for example, one or more hundreds of relatively small openings spaced closely together (i.e., a mesh). The openings expose the substrate to the environment exterior to the hollow enclosure, allowing metal ion to be released from the substrate upon exposure to water and/or heat. Accordingly, the openings of the hollow enclosure allow metal ions from the substrate to be released into the wash water or tumble dryer.

In some embodiments of the articles of the disclosure, the substrate is provided in the enclosure as either dry or moist. The substrate may be moistened with, for example, water, alcohol, silicone fluids, and the like, and packaged in an air-tight package that is opened just prior to use. The moisture of the substrate can evaporate upon exposure to heat and/or air in the dryer while releasing the metal ion into the environment. In another example, the substrate may be dry, such that the substrate could be moistened by the addition of water some time before the addition of the article to a tumble dryer. In yet another example, the substrate may be dry but absorb moisture from the wet textiles added to the dryer. The moistened substrate then dries along with the textiles while releasing the metal ion. In yet another example, the substrate may be dried, such that the substrate could is moistened by the water contained in a wash basin. In yet another example, the substrate may be dried, such that it releases the metal ion through steam and or humidity.

In one aspect, the hollow enclosure is reusable and the substrate is replaceable. In this aspect, the substrate can be removed from the enclosure and discarded after a laundry cycle. An unused substrate can then be placed into the enclosure for use in the next laundry cycle. The enclosure may have an opening that allows for replacement of the substrate, or the enclosure may itself be opened by a mechanism such as threads, hinges, etc. Also, the substrate may be in the form of a replaceable, cartridge-like insert. In some embodiments, the entire article is disposable (i.e., one-time use).

As described above, the substrate contains a core composition comprising a metal ion having antimicrobial activity, for example, silver ion or copper ion. Dissociable ionic compounds capable of providing the metal ion are well known. The amount of the compound and ion can be accommodated to address the size of the wash basins and laundry loads. In addition, the amount of ion may be adjusted to accommodate the release rate of metal ions from the core composition. An amount of silver ion imparted to the textiles at the end of the laundry process in order to provide an antimicrobial effect is in the range of about 1 mg to about 100 mg per kilogram of textile, for instance 1, 2, 3, 4, 5, 6, 7, 8, 9, 10, 12, 14, 16, 18, 20, 25, 30, 35, 40, 45, 50, 60, 70, 80, 90, and 100 mg/Kg (and fractions thereof). The efficiency of the transfer of the ion from the substrate to the textile during the treatment process will determine the amount of ion necessary in the substrate at the beginning of the process.

Accordingly, in various embodiments the amount of metal ion can be in the range of about 10 to about 100 mg/kg, depending on the anticipated size of a laundry load. As one example, in a typical household washer having a laundry basin holding about 10 to 20 L of water and a laundry load of about 10 kg of textiles, an amount of silver nitrate in the core composition could range from about 16 mg to about 316 mg, which contains about 10 mg to about 200 mg silver ion, for instance about 10, 20, 30, 40, 50, 60, 70, 80, 90, 100, 110, 120, 130, 140, 150, 160, 170, 180, 190 or 200 mg silver ion. The amount of silver nitrate can be adjusted to address the variations in laundry sizes and substrates as described herein. Similar amounts can be used for other metallic ionic compounds to provide metal the ion in an amount that provides anti-microbial efficacy to the treated textile.

In one embodiment where the metal ion is silver and the substrate is moist, the substrate contains an aqueous solution of silver ion. The concentration of silver ion dissolved in the aqueous solution could range from about 50 ppm to about 1000 ppm, e.g., about 75 ppm to about 900 ppm, or about 125 ppm to about 800 ppm, or about 150 ppm to about 700 ppm, or about 175 ppm to about 600 ppm, or about 200 ppm to about 500 ppm, or about 225 ppm to about 400 ppm, or about 250 ppm to about 350 ppm. The amount of silver ion can be adjusted to accommodate the size and release profiled of the substrate, and to accommodate large or small tumble dryers and laundry loads.

In some embodiments, the core composition further includes a second compound. The core composition may therefore be a combination of the ionic compound and the second compound. In certain such embodiments, the second compound reduces the concentration of the metal ion from the ionic compound (e.g. silver ion from silver nitrate) in the wash water so that it is less concentrated and less toxic. For instance, the second compound may have "binding" properties that limit the availability of free metal ions in solution by providing counterions with which metal ions have a low dissociation constant. The second compound may also control the rate of release of the metal ions. In certain such embodiments, the majority of the metal ions are prevented from being released early in the wash cycle. Because of some metals ion's, such as silver ion's, strong attraction for fabric, the rate of ion release into a wash cycle can be controlled to prevent inconsistent distribution of the metal ion throughout a laundry load that may result from an article's complete dose of the metal ion becoming immediately available and adhered to fabrics in the vicinity of the article in the laundry load.

The core composition may further include a third compound, which may be water soluble and includes an adhesive/cohesive material to control the rate at which the ionic compound and, if present, the second compound dissolve in water. It may be desired that the ions be delivered later in a wash cycle (for example in the rinse cycle, rather than the detergent cycle) to minimize the number of ions that may be washed out before the wash cycle is completed, and the third compound to ensure that enough silver is present at the appropriate time during a desired portion (wash, rinse, dry) of a laundry cycle.

In various embodiments of the disclosure, the release of the metal ions is achieved by first impregnating the substrate with a mixture of the ionic compound and, optionally, the second compound and/or the third compound. For example, in certain such embodiments, the substrate may be soaked in a solution containing the core composition and allowed to dry. After the impregnated materials have dried, a layer of the third compound with both cohesive and adhesive properties is applied to create an outer layer on the substrate. The effect of this outer layer in the wash is to dissolve slowly thereby delaying the point in time where the underlying first compound and second compound are exposed to the wash water. When the third compound is used as an outer coating, the underlying first and second compounds are not exposed until the third compound is fully (or mostly) removed. Water soluble polymers such as poly-vinyl alcohols and poly acrylamide are examples of the type of compounds suitable for the third compound.

In another other embodiment, the third compound may be mixed with the first compound and the compound to form one core composition that has the potential to simplify the manufacturing process by impregnating the substrate in one application as opposed to the two-step process described above.

A variety of compounds may be suitable for use as the second compound in accordance with the articles of the disclosure. The second compound can be ionic or non-ionic. Examples of non-ionic compounds include ligands such as amines, phosphines, benzoic acid, and phthalic acid; and organic solvents and non-ionic surfactants including long-chain alcohols such as cetyl, stearyl, and oleyl alcohol; polyethers such as polyethylene glycol, polypropylene glycol, polyoxymethylene, polyethylene oxide, and polypropylene oxide; glucoside alkyl ethers; glycerol alkyl esters; and polysorbates.

Examples of ionic compounds that may be suitable for the second compound are shown in Table 1, which provides a non-exclusive list of useful compounds that are arranged in descending order of dissociation constant between silver ion and the counterion of the second compound. In general, the lower the dissociation constant, the lower the concentration of available silver ion in solution (i.e., solubility). For example, compounds such as sodium nitrate and sodium fluoride can be mixed with silver nitrate to reduce the total amount of silver in the core composition. As shown in Table 1, this composition would be the quickest to dissociate and make silver ion available in the wash bath. In other examples, mixture with compounds such as sodium chloride and sodium sulfate will not only reduce the total amount of silver in the core composition, but will provide counterions (e.g., $Cl^-$, $SO_4^{2-}$) that will more strongly associate with silver, limiting the concentration of available silver ion in the wash bath. In such examples, as available silver ion is removed from solution (e.g., through deposition onto clothing or textile), more silver will dissociate from the second counterion and become available as silver ion.

TABLE 1

| Binder | Binding Ion | Dissociation Constant | Silver Ion Availability | Counterion formula | Solubility Limit (g/100 mL) |
|---|---|---|---|---|---|
| Sodium Nitrate | Nitrate | ↑ | | $AgNo_3$ | 256 |
| Sodium Fluoride | Fluoride | | | AgF | 100 |
| Potassium Sulfate, Sodium Sulfate | Sulfate | | | $Ag_2SO_4$ | 0.83 |
| Sodium Carbonate | Carbonate | | | $Ag_2CO_3$ | 0.0032 |
| Sodium Chloride | Chloride | | | AgCl | 1.60E−04 |
| Sodium Sulfide | Sulfide | ↓ | | $A_g2S$ | 6.21E−16 |

Sodium sulfate is already used as a filler in powdered laundry detergents, so its safety and efficacy is well established. In addition to the compounds shown in Table 1, compounds that provide other ions, such as bromide and iodide ions may be used (e.g., sodium or potassium bromide or iodide). In various embodiments, the dissociation constant of the metal ion and the first counterion is equal to or greater than the dissociation constant of the metal ion and the second counterion.

An example of how the ion exchange process might work with silver nitrate as the ionic compound and sodium sulfate as the second compound is presented below:

1)

$$2AgNO_{3(aq)} \rightleftharpoons 2Ag^+_{(aq)} + 2NO_3^-_{(aq)}$$

$$Na_2SO_{4(aq)} \rightleftharpoons 2Na^+_{(aq)} + SO_4^{2-}_{(aq)}$$

2)

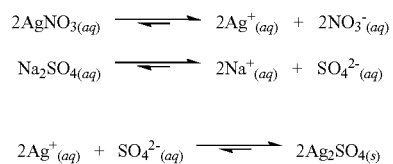

In the first step, silver nitrate ($AgNO_3$) would be mixed with sodium sulfate ($Na_2SO_4$) to provide a core composition. Once in the presence of wash water within the article, a solution containing ions of silver ($Ag^+$), sodium ($Na^+$), nitrate ($NO3^-$) and sulfate ($SO_4^{2-}$) is formed. In a second step, silver and sulfate ions strongly associate to form silver sulfate ($Ag_2SO_4$), limiting the availability of silver ions in solution. When silver sulfate is in the presence of wash water, silver and sulfate ions will slowly dissociate and be released into the wash bath. As silver ions are deposited onto the clothing or textiles, more silver will dissociate from sulfate, becoming available as silver ions. Alternatively, silver (from silver sulfate) can come into contact with and be deposited directly onto clothing or textiles, e.g., in a dryer.

Alternatively, silver sulfate may be substituted for the two ingredients silver nitrate and sodium sulfate in the core composition. This same substitution option applies to all of the other compounds listed in Table 1. The difference is that only Step 2 for the various compounds listed would occur in the presence of the wash water.

Similarly, sodium carbonate and potassium sulfate will form silver compounds that are less soluble than silver nitrate. The chemical process for these two compounds with silver nitrate are shown below:

1)

Sodium Carbonate

2)

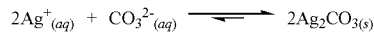

1)

Potassium Sulfate

2)

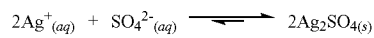

In some embodiments is disclosure, the substrate may further include a number of materials or compounds that provide a benefit to the textile. For instance, the substrate may include, a fragrance, a laundry softener, or a combination thereof. In some embodiments, the substrate may include a lubricant or positively charged material capable of providing an anti-static effect in, e.g., a tumble dryer.

Another aspect of the disclosure described herein is a method for treating a textile by loading the textile into a wash basin (i.e., of a conventional washer extractor) containing water and loading the article of the disclosure. During the wash cycle, the article releases metal ion which becomes attached to the textile. At the conclusion of a wash cycle, when a mechanical drying cycle is used, the article may be removed along with the wet clothing or linens and moved to the dryer. In the dryer, additional metallic ions may be deposited from the article onto the clothing or linens. Finally, after the drying cycle is complete, as the dried clothes are removed and separated, the article can be removed and thrown away in the trash. By that time, it is anticipated that all or most of the metallic compound will have left the article.

Another aspect of the disclosure described herein is a method for treating a textile by loading the textile into a laundry dryer along with the article of the disclosure. Such a method does not require a significant amount of water or a wash basin, and produces little or no effluent. In some embodiments of the method, the substrate is moist. In other embodiments of the method, the substrate of the article is not moist, in which case the method disclosed herein may further include moistening the substrate before loading the article into the dryer. In other embodiments of the method, the substrate of the article is not moist, in which case the method disclosed herein may include the loading of a wet textile into the dryer.

In some embodiments of the method, the item loaded into a dryer or a wash basin containing water may include any textile or laundered good such as, for example, shirts, pants, socks, sheets, drapes, pillows, towels, blankets, undergarments and the like. In some embodiments of the method, the item loaded into a dryer may include any non-laundered good (e.g., goods that cannot be laundered in a conventional washing machine), such as, for example, athletic gear, athletic pads, ropes, shoes, and the like. These goods can be treated in a drying cycle. In some embodiments, the goods are wet or moist. In some embodiments, the goods are dry when entering the dryer.

EXAMPLES

The Examples that follow are illustrative of specific embodiments of the disclosure, and various uses thereof. They are set forth for explanatory purposes only, and are not to be taken as limiting the disclosure.

Example 1

Laundry Orb in Dryer 47 mL of 317 ppm silver ion was added to a polyurethane sponge enclosed in a plastic hollow enclosure with a 3.5 inch diameter having 31 evenly spaced circular openings with a diameter ranging from 3/32 inches to 3/16 inches. The article was included in a wet load of textiles (dry weight 6.7 lb) for a tumble dry cycle with the settings "Heavy Duty", "High Temperature" (120-155 deg. F.), and "More dry" for 55 minutes in a standard home-use dryer. Three separate runs yielded silver content uptakes by the textiles of 1.2, 6.2, and 3.7 mg/kg, for an average silver content uptake of 3.7 mg/kg. The article was also included in a dry load of textiles for a tumble dry cycle using the same parameters as with a wet load of textiles. Three separate runs yielded silver content uptakes by the textiles of 0.9, 1.0 and 4.8 mg/kg, for an average silver content uptake of 2.2 mg/kg.

Example 2

Laundry Orb in Washer 55 mL of 317 ppm silver ion was added to a mixture of cotton textile and polyester textile enclosed in a plastic hollow enclosure with a 3.5 inch diameter comprising 31 evenly spaced circular openings with a diameter ranging from 3/32 inches to 3/16 inches. The article was included in a load of textiles with a dry weight of 6.7 pounds for a wash cycle with 21 gallons of water with "normal settings" and "cool" temperature in a standard home use washing machine for 55 minutes which includes the following steps: fill 10.5 minutes, agitation 14.5 minutes, drain/spin 6 minutes, fill 10.5 minutes, agitation 5.5 minutes, and drain/spin 8 minutes. The cycle yielded a silver content uptake by the textiles of 1.33 mg/kg.

Although preferred embodiments of the disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

The invention claimed is:

1. An article for use in treating a textile in a laundry cycle with an antimicrobial compound, wherein prior to using the article to treat the textile in the laundry cycle, the article comprises:
    (a) a porous substrate comprising a fabric, wherein the substrate comprises one or more sheets; and
    (b) a core composition comprising a metal ion having antimicrobial activity and a first counterion, wherein the core composition is releasably associated with the substrate, and wherein the core composition further comprises a second compound comprising a second ion and a second counterion, wherein the dissociation constant of the metal ion and the first counterion is greater than the dissociation constant of the metal ion and the second counterion, and wherein the metal ion is different than the second ion.

2. The article of claim 1, wherein the metal ion is silver ion.

3. The article of claim 1, wherein the metal ion is copper ion.

4. The article of claim 1, wherein the fabric comprises at least one of cotton and polyester.

5. The article of claim 1, wherein the substrate further comprises a sponge.

6. The article of claim 5, wherein the sponge comprises at least one of polyethylene, polypropylene, and polyurethane.

7. The article of claim 1, wherein the substrate further comprises an open cell foam plastic.

8. The article of claim 7, wherein the open-cell foam plastic comprises polyethylene, polypropylene and combinations thereof.

9. The article of claim 7, wherein open cell foam plastic has at least one of the following properties: (a) pore size from about 10 µM to about 50 µM, and (b) pore density of about 10-30 pores per inch.

10. The article of claim 1, wherein the substrate is moist.

11. The article of claim 1, further comprising a hollow enclosure encasing the substrate, wherein the hollow enclosure comprises one or more openings that expose the substrate to an environment exterior to the enclosure.

12. The article of claim 11, wherein the hollow enclosure comprises a hard plastic.

13. The article of claim 11, wherein the hollow enclosure is spheroidal or spherical.

14. The article of claim 1, wherein the second counterion is selected from nitrate, fluoride, sulfate, carbonate, chloride, bromide, iodide, and sulfide.

15. The article of claim 1, wherein the core composition further comprises a third compound comprising an adhesive/cohesive material.

16. The article of claim 15, wherein the substrate is coated with a third compound comprising an adhesive/cohesive material.

17. The article of claim 1, wherein the fabric comprises natural fibers.

18. The article of claim 1, wherein the fabric comprises synthetic fibers.

19. The article of claim 1, wherein the laundry cycle comprises at least one of a washing cycle, a rinsing cycle, and a drying cycle.

20. A method for treating a textile in a laundry cycle, comprising
    loading the textile and the article of claim 1 into a wash basin containing water, and
    washing the textile in the presence of the article.

21. The method of claim 20, wherein the washing comprises at least one of a wash cycle and a rinse cycle.

22. A method for treating a textile, comprising
    loading the textile and the article of claim 1 into a tumble dryer, and
    exposing the textile and the article to at least one of heat and air in the dryer.

23. The method of claim 22, further comprising drying the textile.

24. The method of claim 22 comprising providing moisture to the substrate of the article before loading the article into the dryer.

25. The method of claim 22, wherein the textile is a non-laundered good.

26. The method of claim 22, wherein the textile and the article are dry when loaded into the dryer.

27. The method of claim 22, further comprising based on exposing the article to at least one of heat and air in the dryer, releasing the metal ion and exposing the textile to the released metal ion.

* * * * *